United States Patent [19]

Zikria

[11] Patent Number: 5,704,358
[45] Date of Patent: Jan. 6, 1998

[54] METHOD AND APPARATUS FOR DIAGNOSING CAPILLARY LEAK

[75] Inventor: Bashir A. Zikria, Norwood, N.J.

[73] Assignee: The Trustees of Columbia University in the City of New York, New York, N.Y.

[21] Appl. No.: 344,334

[22] Filed: Nov. 22, 1994

[51] Int. Cl.$^6$ .................................................. A61B 6/00
[52] U.S. Cl. ............................ 128/654; 128/659; 128/630
[58] Field of Search ................................. 128/630, 637, 128/638, 654, 659, 668, 691, 898; 600/4, 5

[56] References Cited

U.S. PATENT DOCUMENTS

| | | |
|---|---|---|
| 4,994,444 | 2/1991 | Zikria . |
| 5,024,231 | 6/1991 | Fledschuh et al. ............. 128/654 |

OTHER PUBLICATIONS

Fleck, A., et al., Increased Vascular Permeability: A Major Cause of Hypoalbuminaemia In Disease and Injury. The Lance (1985) 1 (8432): 781–784 (Exhibit C).

Shippy, C. R., et al., Reliability of Clinical Monitoring to Assess Blood Volume in Critically Ill Patients. Critical Care Medicine (1984) 12: 107–112 (Exhibit E).

Gosling, P., et al. Generalized Vascular Permeability and Pulmonary Function in Patients Following Serious Trauma. The Journal of Trauma (1994) 36: 477–481 (Exhibit D).

Shoemaker, W.C., Pathophysiology and Fluid Management of Postoperative and Post–Traumatic ARDS. Assessment of Blood Volume Deficit. Shoemaker, W. C., et al. eds. Textbook of Critical Care. Philadelpphia: Saunders (1989), p. 626 (Exhibit F).

Shoemaker, W. C., et al. eds. Textbook of Critical Care. Philadelphia: Saunders (1989), p. 626 (Exhibit F).

Valeri, C.R., et al. Limitations of Measuring Blood Volume With Iodinated I 125 Serum Albumin. Archives of Internal Medicine (1973) 132: 534–538 (Exhibit G).

Volemetron. Pathol. Biol. (1967) 15 (9): 566–567 (Exhibit H).

*Primary Examiner*—Robert Nasser
*Attorney, Agent, or Firm*—John P. White

[57] ABSTRACT

This invention provides a method for determining the presence of capillary leak in a subject which comprises (a) introducing into the subject's circulation a pharmaceutically-acceptable solution comprising biodegradable, nontoxic, macromolecules, which macromolecules are smaller than endothelial gaps in capillaries of a subject having capillary leak, and each of which macromolecules is labeled with a detectable marker; (b) obtaining a sample of blood from the subject; (c) quantitatively measuring the detectable marker in the sample; (d) repeating steps (b) and (c) at a plurality of suitably spaced points in time; and (e) comparing the quantities of detectable marker so measured so as to ascertain a change in the quantity of detectable marker in the subject's circulation over time, the change being indicative of the presence of capillary leak, thereby determining the presence of capillary leak in the subject. The subject invention also provides an apparatus for displaying the quantity of detectable marker in a subject's circulation over time after introducing into the subject's circulation a pharmaceutically-acceptable solution comprising biodegradable, nontoxic macromolecules, which macromolecules are smaller than endothelial gaps of capillaries in a subject having capillary leak, and each of which macromolecules is labeled with a detectable marker, which apparatus comprises (a) means for obtaining samples of blood from the subject at a plurality of points in time; (b) means for quantitatively measuring the detectable marker in the sample obtained at each time point; and (c) means for displaying the quantities so measured. The aforementioned apparatus of the subject invention is useful for diagnosing capillary leak.

21 Claims, 3 Drawing Sheets

METHOD AND APPARATUS FOR DIAGNOSING CAPILLARY LEAK

Throughout this application various publications are referenced by arabic numerals within parentheses. Full citations for these publications may be found at the end of this application, preceding the claims. The disclosures of these publications in their entireties are hereby incorporated by reference into this application in order to more fully describe the state of the art to which this invention pertains.

Current scientific literature reveals that inflammatory mediators initiate a biochemical chain of events that increase capillary permeability. Under such circumstances the separation of capillary endothelial junctions into gaps cannot keep infused colloids such as serum albumin, Dextran-40, and particular intracapillary fluids within the vessel.

Colloids such as serum albumin escape into the interstitium creating a nonfunctional "third space", the volume of which increases as albumin leakage increases. This leakage widens capillary-cellular distances, creating problems of poor diffusion and transport between the circulatory system and the functional cells and the capillaries. Consequently, less oxygen and energy substrates are able to enter the cell and less carbon dioxide and its acid by-products are able to leave. These events result in cellular anoxia, a cellular energy deficit, acidosis, and possibly sequential organ failure.

In the past, others have approached the problem of albumin leakage and the concurrent creation of a third space through chemical or pharmacological means. U.S. Pat. No. 4,994,444, Zikria, issued Feb. 19, 1991, which is hereby incorporated by reference into the subject application, describes a method to solve the problem of capillary endothelial gaps which involves using natural or synthetic macromolecules as sealants to inhibit the escape of albumin and other macromolecules. These macromolecules are effective because their configuration prohibits their escape through the enlarged capillary endothelial junctions, i.e. the endothelial gaps.

The above-described phenomenon of increased capillary permeability has been termed "capillary leak", and also "clinical capillary leak syndrome". Capillary leak, which results from certain inflammatory mediators, occurs primarily in the 10 to 50 micrometer-diameter postcapillary (pericytic) venules. The mechanism of this leakage was demonstrated almost two decades ago for histamine, serotonin, and bradykinin by electron microscopic studies, which were confirmed in vivo.(1, 2) The endothelial cells in the postcapillary venules have been shown to contract and pull away from each other (3), producing endothelial cell gaps, i.e. endothelial gaps. These endothelial gaps vary from organ to organ, with the tight blood-brain barrier interface constituting one end of the spectrum and the sinusoids of liver the other. It is the modification of these cell junctions following insult that allows the escape of albumin and certain globulins, serum's most important hydrophilic macromolecules, into the interstitium. The entry of albumin with 200 ionic charges and a net charge of −18 (4), and other protein macromolecules into the narrow interstitium, turns this compartment into a nonfunctioning space, the "third space." (5) Problems of oxygen and energy substrate diffusion into cells and clearance of carbon dioxide and other waste products from cells may be the harmful consequences. The resulting interstitial and cellular swelling increases tissue pressures until the lymphatic draining system of the interstitium is collapsed. Ensuing congestion may result in venous and arteriolar occlusion and ischemic necrosis.

Diagnosis of capillary leak would be valuable in determining whether to treat a subject according to described methods for treating capillary leak. However, few such methods presently exist. Existing methods include quantitative determination of urinary albumin and total protein spillage. However, such methods may be disadvantageously slow, considering that the earlier the diagnosis of capillary leak, the better may be the likelihood of successful treatment.

It is proposed herein that disappearance curves of FITC dextran 150 (polymeric dextran having an average molecular weight of about 150,000 daltons) be used in diagnosis of clinical capillary leak syndrome. Because FITC-albumin leaks in critically ill patients (presumable in the presence of some degree of capillary leak syndrome), with determination of its dilution curve by a fluorometer, the rate of capillary leak can be estimated.

Once it is possible to determine whether patients have generalized capillary leakage, i.e. clinical capillary leak syndrome, the therapeutic dilemma of using crystalloids versus colloids by and large may be resolved. Without knowing a patient's capillary integrity, while administration of crystalloids may not harm the patient severely, administration of present colloids (such as plasma, albumin, dextran 40 and 70, and Hespan), may severely compromise their recovery from shock syndromes, trauma, sepsis, and toxemias. These colloids, having molecules small enough to leak into interstitial space, would make the third space phenomenon more intractable.

SUMMARY OF THE INVENTION

This invention provides a method for determining the presence of capillary leak in a subject which comprises (a) introducing into the subject's circulation a pharmaceutically-acceptable solution comprising biodegradable, nontoxic, macromolecules, which macromolecules are smaller than endothelial gaps in capillaries of a subject having capillary leak, and each of which macromolecules is labeled with a detectable marker; (b) obtaining a sample of blood from the subject; (c) quantitatively measuring the detectable marker in the sample; (d) repeating steps (b) and (c) at a plurality of suitably spaced points in time; and (e) comparing the quantities of detectable marker so measured so as to ascertain a change in the quantity of detectable marker in the subject's circulation over time, the change being indicative of the presence of capillary leak, thereby determining the presence of capillary leak in the subject.

The subject invention also provides an apparatus for displaying the quantity of detectable marker in a subject's circulation over time after introducing into the subject's circulation a pharmaceutically-acceptable solution comprising biodegradable, nontoxic macromolecules, which macromolecules are smaller than endothelial gaps of capillaries in a subject having capillary leak, and each of which macromolecules is labeled with a detectable marker, which apparatus comprises (a) means for obtaining samples of blood from the subject at a plurality of points in time; (b) means for quantitatively measuring the detectable marker in the sample obtained at each time point; and (c) means for displaying the quantities so measured. The aforementioned apparatus of the subject invention is useful for diagnosing capillary leak.

This animal died in a semicomatose state six hours later. The char clearly shows a steep slope which indicates generalized and massive capillary leak in spite of resuscitation by four times the volume of shed blood with crystalloid (Ringer's lactate).

Figure 3:
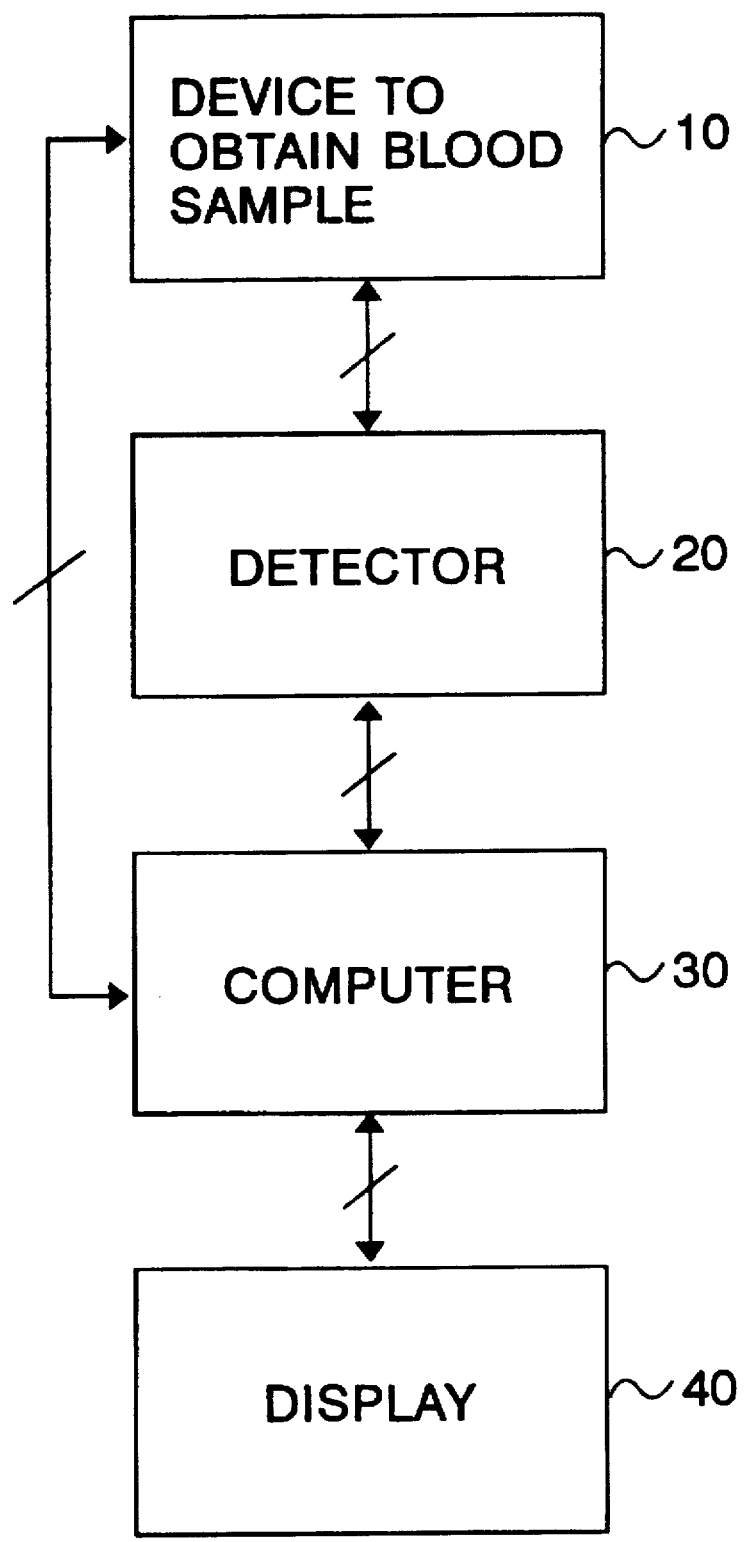

FIG. 3 An embodiment of an apparatus for measuring and displaying capillary leak. FIG. 3 depicts a device for obtaining samples of blood from a subject (10), a detector of the marker in said sample (20), a computer to calculate the presence of capillary leak based on the quantity of marker detected (30), and a display to indicate the presence of capillary leak (40).

DETAILED DESCRIPTION OF THE INVENTION

The subject invention provides a method for determining the presence of capillary leak in a subject which comprises (a) introducing into the subject's circulation a pharmaceutically-acceptable solution comprising biodegradable, nontoxic, macromolecules, which macromolecules are smaller than endothelial gaps in capillaries of a subject having capillary leak, and each of which macromolecules is labeled with a detectable marker; (b) obtaining a sample of blood from the subject; (c) quantitatively measuring the detectable marker in the sample; (d) repeating steps (b) and (c) at a plurality of suitably spaced points in time; and (e) comparing the quantities of detectable marker so measured so as to ascertain a change in the quantity of detectable marker in the subject's circulation over time, the change being indicative of the presence of capillary leak, thereby determining the presence of capillary leak in the subject.

In the method of the subject invention, the macromolecules in the solution injected into the subject's circulation, leak from the subject's capillaries over time if the endothelial junctions in the subject's capillaries are equal to or larger than endothelial gaps in the capillaries of a subject suffering from capillary leak. Accordingly, any change in the presence of the macromolecules resulting from such leak indicates that the subject is suffering from capillary leak. The detectable marker labelling each macromolecule permits changes in the presence of the macromolecules to be ascertained. In one embodiment of the subject method, the change indicative of the presence of capillary leak is a decrease in the quantity of detectable marker. In a further embodiment of the method of the subject invention, the change indicative of the presence of capillary leak is an initial increase in the quantity of detectable marker followed by a decrease in the quantity of detectable marker. The initial increase in the quantity of detectable marker results from hemoconcentration of the macromolecules in the subject's circulation.

For purposes of the subject invention, a pharmaceutically acceptable solution is any solution which is not toxic to the subject into which the solution is injected. Pharmaceutically acceptable solutions useful in the subject method may be formulated using any standard pharmaceutically accepted carrier known to those of ordinary skill in the art. Examples of such standard carriers include, but are not limited to, saline, phosphate buffered saline solution, water, emulsions such as oil/water emulsions or triglyceride emulsions, and various types of wetting agents. A suitable pharmaceutically acceptable carrier may be selected taking into account the mode chosen for introducing the solution into the subject's circulation.

The above-described method of the subject invention may be used to diagnose capillary leak in any subject. In one embodiment, the subject is a mammal. In a further embodiment, the subject is a human.

In another embodiment of the method of the subject invention, the subject is predisposed to capillary leak. Conditions predisposing a subject to capillary leak are well known. For example, a subject who has suffered trauma and/or anoxia is predisposed to capillary leak. As used herein, trauma indicates any bodily injury resulting from some external condition or conditions. Examples of trauma which predispose a subject to capillary leak include burns, shock, ischemia, organ transplantation, complications from a surgical technique or techniques, sepsis, poisoning, or anaphylaxis (an allergic reaction). For example, sepsis is associated with "Toxic Shock Syndrome". Thus, a subject suffering "Toxic Shock Syndrome" would be predisposed to capillary leak. As another example, certain poisonings, such as an overdose of salicylic medications, or poisoning by rattle snake venom, are known to result in severe capillary leak. Thus, subjects so poisoned would be predisposed to capillary leak. As a further example, cardiopulmonary bypass surgery is known to cause severe capillary leak in children. Thus, a child who has undergone a cardiopulmonary bypass would be predisposed to capillary leak.

Also, certain other conditions, such as Hyaline Membrane Disease and Systemic Capillary Leak Syndrome (a familial condition), are known to predispose a subject to capillary leak. Accordingly, in one embodiment of the method of the subject invention, the subject possesses a genetic condition predisposing the subject to capillary leak.

Moreover, adverse side effects of certain therapies are known to predispose a subject to capillary leak. Accordingly, in another embodiment of the method of the subject invention, the subject has undergone a therapy predisposing the subject to capillary leak. One therapy which predisposes a subject to capillary leak is immune therapy, such as by treatment with interleukin-2 or treatment with lymphokine activated killer cells (LAK). Immune therapy is useful, for example, for treating cancer in a subject. Another therapy which predisposes a subject to capillary leak is chemotherapy and/or bone marrow transplant. Other therapies which predispose subjects to capillary leak are known to those of ordinary skill in the art.

Any method of introducing the solution into the subject's circulation may be used in the method of the subject invention. Methods for introducing a solution into a subject's circulation are well known in the art and include, but are not limited to, introduction by intravenous injection.

The macromolecules in the above-described method are biodegradable and nontoxic to the subject into which they are introduced, and are smaller than endothelial gaps in capillaries of a subject having capillary leak.

Factors permitting a macromolecule to leak through the endothelial gaps include the size and the shape of the macromolecule. Macromolecules of any shape, including fibrous shape and globular shape, may be used in the subject method, provided the macromolecules are able to pass through endothelial gaps. In one embodiment of the method of the subject invention, the macromolecules are globular in shape. Globular macromolecules having a molecular weight of from about that of albumin (a globular molecule having a molecular weight of about 69,000 daltons) to about 150,000 daltons (the size at which macromolecules begin to get stuck in leaky capillaries and hence seal the leaky capillaries) are of suitable size to pass through endothelial gaps. Accordingly, in one embodiment of the subject invention wherein the macromolecules are globular polymeric macromolecules, they have an average molecular weight of from about 69,000 daltons to about 150,000 daltons. Globular polymeric molecules having an average molecular weight of from about 69,000 daltons to about 150,000 daltons are well known and readily available to those of ordinary skill in the art. Such macromolecules include, but are not limited to, macromolecules derived from dextran. Nonpolymeric globular macromolecules, such as albumin, may be useful in the subject invention.

In the above-described method of the subject invention, any detectable marker may be used to label the macromolecules in the solution introduced into the subject's circulation. Detectable markers are well known in the art. The particular detectable marker selected for use will depend on factors known to those of ordinary skill in the art, including, but not limited to, the toxicity of the marker to the particular subject, and the expense and ease by which the marker may be detected in the subject. Examples of detectable markers which may be used in the method of the subject invention include, but are not limited to fluorophores, such as fluorescein isothiocyanate (FITC); chromophores; and radioactive substances, such as radioactive iodine or chromium. In one embodiment of the subject method, the macromolecules which are each labeled with a detectable marker comprise FITC dextran 150 (polymeric dextran having an average molecular weight of about 150,000 daltons and labeled with fluorescein isothiocyanate, available from Sigma Chemical Company, St. Louis, Mo.). In another embodiment, the macromolecules which are each labeled with a detectable marker comprise FITC-albumin.

The subject invention also provides an apparatus for displaying the quantity of detectable marker in a subject's circulation over time after introducing into the subject's circulation a pharmaceutically-acceptable solution comprising biodegradable, nontoxic macromolecules, which macromolecules are smaller than endothelial gaps of capillaries in a subject having capillary leak, and each of which macromolecules is labeled with a detectable marker, which apparatus comprises (a) means for obtaining samples of blood from the subject at a plurality of points in time; (b) means for quantitatively measuring the detectable marker in the sample obtained at each time point; and (c) means for displaying the quantities so measured. Such an apparatus is useful for diagnosing capillary leak in a subject by providing a convenient visual display of changes in the presence of tracer macromolecules in the subject's circulation.

Any means for obtaining a sample from a subject may be used in the apparatus of the subject invention, and such means are well-known in the art. The means for quantitatively measuring the detectable marker in the apparatus of the subject invention will be selected based on the particular detectable marker used. For example, if the detectable marker is a flourophore, the means for quantitatively measuring the marker may be a fluorometer. Means (c) of the subject apparatus may comprise a computer and appropriate software for displaying changes in the presence of the detectable marker in the form of a graph. Moreover, the apparatus of the subject invention, may be advantageously designed for bedside use.

This invention will be better understood from the Examples in the "Experimental Details" Section which follows. However, one skilled in the art will readily appreciate that the specific methods and results discussed are merely illustrative of, and are not intended to, nor should they be construed to, limit the invention as described more fully in the claims which follow thereafter.

EXPERIMENTAL DETAILS

Protocol For Treatment of Irreversible Hemorrhagic Shock and Determination of Capillary Lear and the Blood Volume Introduction.

Following severe hemorrhagic shock in Wigger's model, even after total replacement of shed blood plus 10% crystalloids or colloids, death becomes inevitable. This phenomenon, initially reproduced in dogs and more recently in rats, is called "Irreversible Shock". This state of irreversibility is very similar to that seen in critically ill patients in ICU units. This irreversibility initially appears to be related to the development of a generalized "capillary leak", which may also be called "Clinical Capillary Leak Syndrome", in patients. Since it has been demonstrated that hydroxyethyl starch macromolecules (HES-Pz) diminish the capillary leakage following ischemia-reperfusion injury in isolated organs of rats, dogs, and hamsters, the systemic capillary leakage in the hemorrhagic shock model may also be significantly reduced by HES-Pz. Therefore, it may be possible to reverse the so called "irreversible shock".

Materials and Methods.

Sprague-Dawley rats (Average weight-350 g) under sodium pentobarbital (50 mg/Kg) underwent femoral arterial catheterization with a 3-way stopcock polypropylene (PE-50, 0.58 mm ID). MAP was monitored with Millar transducers. Blood was drawn by heparinized syringes to bring MAP to 30–40 mm Hg. Up to 90 minutes, the MAP was maintained at these pressures by infusing or withdrawing the necessary amount of blood. At 90 minutes shock period, animals were resuscitated with their own shed blood, which produces about 40–50% mortality in 24 hours. The following groups were be compared for a) 24 hr. mortality, b) total body weight, c) organ weights and organ potassium an water content (lungs, liver, heart, kidneys and small bowel):

Group I: sham;

Group II: resuscitated with shed blood;

Group III: resuscitated with four times volume of shed blood as Ringer's lactate;

Group IV: resuscitated with shed blood+10% of shed blood as Ringer's lactate;

Group V: resuscitated with shed blood+10% of shed blood as 12% Albumin;

Group VI: resuscitated with shed blood+10% of shed blood as 12% Hespan;

Group VII: resuscitated with shed blood+10% of shed blood as 12% HES-Pz.

Also, the capillary leak that developed in the animal models was studied at 90 minutes by I.V. use of FITC-albumin and FITC dextran 150 (Sigma Chemical Company; St. Louis, Mo.). With a LS-30 Fluorometer, the decay curve of these small fluorescent molecules was determined by determining plasma concentrations of injected tracer at 5, 15 and 30 minutes. By this technique, the extent of capillary leak in the animal models was quantitated (see FIG. 1 and FIG. 2).

Results.

Figure 1:
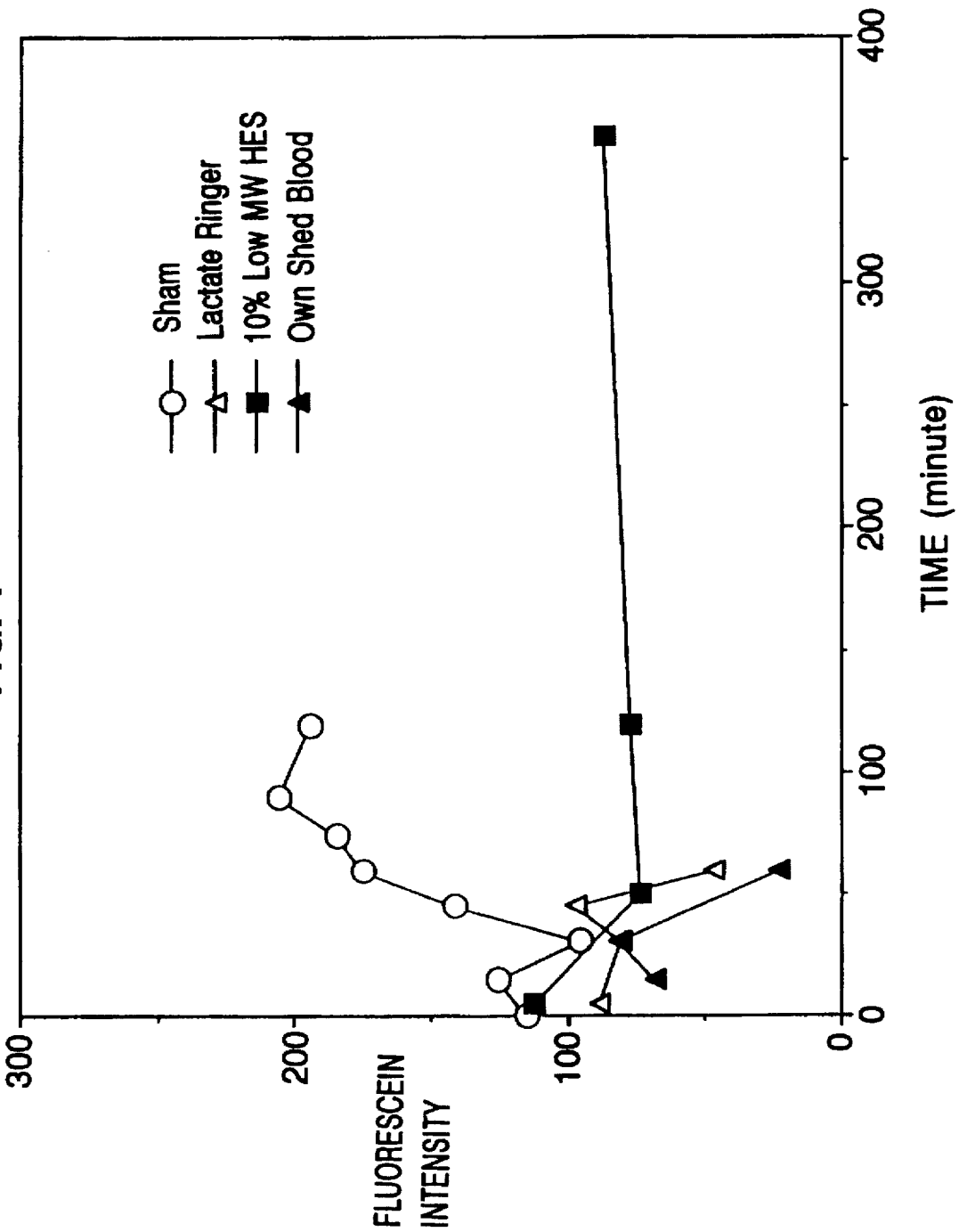
FIG. 1 Fluorescein intensity observed over time in the blood of rats injected with FITC-albumin. Those animals injected with Ringer's lactate or with their own shed blood initially showed hemoconcentration of fluorescein. This initial hemoconcentration was followed by a decrease in the fluorescein intensity, indicating that the FITC labeled molecules were leaking from the animals' capillaries, and thus indicating the presence of capillary leak. In the animals injected with HES-Pz (10% Low MW HES), little or no decrease in fluorescein intensity is observed, indicating that the hydroxyethyl starch molecules have successfully blocked the leakage of the FITC labeled albumin.

FIG. 1 charts the fluorescein intensity observed over time in the blood of the tested animals. As can be seen from FIG. 1, those animals injected with Ringer's lactate or with their own shed blood initially showed hemoconcentration of fluorescein. This initial hemoconcentration was followed by a decrease in the fluorescein intensity, indicating that the FITC labeled molecules were leaking from the animals' capillaries. The hemoconcentration initially observed was most likely due to intravascular fluid leakage preceding the leakage of the FITC labeled macromolecules. In the animals injected with HES-Pz (10% Low MW HES), little or no decrease in fluorescein intensity is observed, indicating that the hydroxyethyl starch molecules have successfully blocked the leakage of the FITC labeled albumin.

Figure 2:
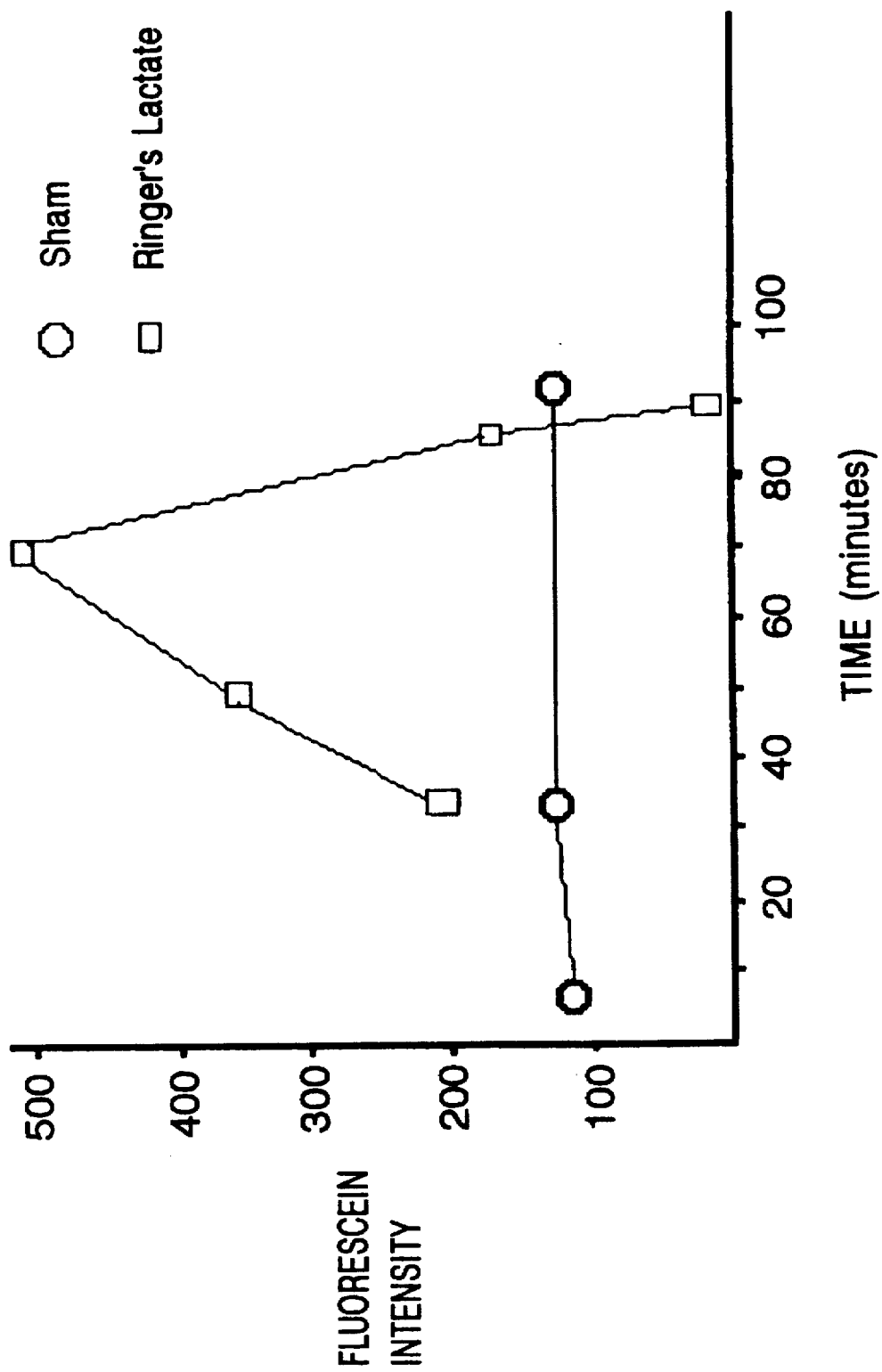
FIG. 2 Determination of capillary leak by FITC dextran 150. In the sham rat since there is no reason for development of capillary leak, the tracer FITC dextran 150 remains fairly constant in its serum concentration indicating the absence of leaky capillaries. In the rat resuscitated by Ringer's lactate, first there is hemoconcentration because of the leakage of intravascular fluids and therefore increasing concentration of the tracer, it being a macromolecule with an average molecular weight similar to albumin. However, after 40 minutes of injection with resuscitation, capillary leak is massive with a precipitous fall in FITC dextran plasma concentration with almost disappearance of the tracer from the plasma.

FIG. 2 illustrates changes in fluorescein intensity over time in animals injected with FITC dextran 150. In the sham rat, since there is no reason for capillary leak, the intensity remains fairly constant. In the animals injected with Ringer's lactate, hemoconcentration is initially observed, followed by a decrease in fluorescein intensity, indicating that the FITC labeled macromolecules are leaking from the animals' capillaries.

The method of the subject invention is particularly useful in bedside diagnoses of capillary leak syndrome in patients. An apparatus for displaying the quantity of detectable marker in a patient's circulation over time after introducing into the patient's circulation a pharmaceutically-acceptable solution comprising biodegradable, nontoxic macromolecules, which macromolecules are smaller than endothelial gaps of capillaries in a subject having capillary leak, and each of which macromolecules is labeled with a detectable marker would assist in such bedside diagnoses.

REFERENCES

1. Arturson G. Microvascular permeability to macromolecules in thermal injury. Acta Physiol Scand. 1979;463:111–122.
2. Joris L Majno G. Corey E J, Levis R A. The mechanism of vascular leakage induced by leukotriene E4: endothelial contraction. Ann Pathol. 1987;126:19–24.
3. Majno G. Shea S M, Leventhal M. Endothelial contraction induced by histamine-type medistors; an electroa microscopic study. J Cell Biol. 1969;42:647–672.
4. Peters Jr T. Serum albumin; adventures of circulating proteins. In: Schecter A. N. Dean A, Goldberg R F, eds. The Impact of Protein chemistry on Biological Sciences. Orlando, Fla: Academic Press Inc; 1984;39–55.
5. Gann D S, Amaral J F, Caldwell M D. Metabolic response to injury, stress, and starvation. In: Drucker W R, Gann D S, Foster R S, Gamelli R L, Pruitt B A, Sheldon G F, eds. Clinical Surgery, St Louis, Mo;CV Mosby Co: 1987;367–368
6. Valeri C R, Cooper A C, Pivacek L E. Limitations of Measuring Blood Volume with Iodinated I-125 Serum Albumin. Arch Int Med 1973; 132: 534
7. Shoemaker W C. Pathophysiology and Fluid Management of Postoperative and Posttraumatic ARDS. Assessment of Blood Volume Deficit. In : Shoemaker W C, Ayers S, Grenvick A, et al. eds. Textbook of Critical Care. Philadelphia : Saunders 1989: 626
8. Shippy C R, Appel P L, Shoemaker W C. Reliability of clinical monitoring to asses blood volume in critically ill patients. Crit Care Med 1984; 12:
9. Shoemaker W C. Shock syndromes as Reperfusion Injuries: Pathophysiology, hemodynamic and oxygen transport patterns, outcome predictions, and therapy. In: Zikria B A, Oz M C, Carlson R W, eds.Reperfusion injuries and Clinical Capillary Leak syndromes. New York: Futura Publishing Co. Inc. 1994
10. Zikria B A, Stanford J, Freeman H P, King T C. A Biophysical Approach to Capillary permeability. surgery 1989: 105: 625
11. Zikria B A, SubbaRao C, Oz M C, et al. Sealing of Capillary Leak in Rat Limb Ischemia-reperfusion Injury. Crit Care Med 1989; 17: 1306
12. Zikria B A, SubbaRao C, Oz M C, et al. Hudoxyethyl Starch macromolecules reduce Myocardial Reperfusion Injury. Arch Surg 1990; 125: 930
13. Oz M C, Zikria B A, McLeod P F. Hydroxyethyl Starch Macromolecules and Superoxide Dismutase Effects on Myocardial Reperfusion Injury. Amer J Surgery 1991; 162: 59
14. Taylor A E, Parker J C, Allison R C, et al. Capillary exchange of fluid and Protein. Leaky Capillary Syndromes. In: Shoemaker W C, Ayers S, Grenvick A, et al., eds Text book of Critical Care. Philadelphia: W B Saunders 1989: 1044

What is claimed is:

1. A method for determining the presence of capillary leak in a subject which comprises:
   (a) introducing into the subject's circulation a pharmaceutically-acceptable solution comprising biodegradable, nontoxic, macromolecules, which macromolecules are smaller than endothelial gaps in capillaries of a subject having capillary leak, and each of which macromolecules is labeled with a detectable marker;
   (b) obtaining a sample of blood from the subject;
   (c) quantitatively measuring the detectable marker in the sample;
   (d) repeating steps (b) and (c) at a plurality of suitably spaced points in time; and
   (e) comparing the quantities of detectable marker so measured so as to ascertain a change in the quantity of detectable marker in the subject's circulation over time, the change being indicative of the presence of capillary leak, thereby determining the presence of capillary leak in the subject.

2. The method of claim 1, wherein the change indicative of the presence of capillary leak is a decrease in the quantity of detectable marker.

3. The method of claim 1, wherein the change indicative of the presence of capillary leak is an initial increase in the quantity of detectable marker followed by a decrease in the quantity of detectable marker.

4. The method of claim 1, wherein the subject is a mammal.

5. The method of claim 4, wherein the subject is a human.

6. The method of claim 1, wherein the subject is predisposed to capillary leak.

7. The method of claim 6, wherein the subject is suffering from trauma and/or anoxia.

8. The method of claim 7, wherein the trauma is associated with a burn, shock, ischemia, organ transplantation, a surgical technique, sepsis, poisoning, or anaphylaxis.

9. The method of claim 6, wherein the subject possesses a genetic condition predisposing the subject to capillary leak.

10. The method of claim 6, wherein the subject has undergone therapy predisposing the subject to capillary leak.

11. The method of claim 10, wherein the therapy comprises immune therapy.

12. The method of claim 10, wherein the therapy comprises chemotherapy.

13. The method of claim 1, wherein the solution is introduced into the subject's circulation by intravenous injection.

14. The method of claim 1, wherein the macromolecules are globular in shape.

15. The method of claim 14, wherein the macromolecules have an average molecular weight of from about 69,000 daltons to about 150,000 daltons.

16. The method of claim 15, wherein the macromolecules are derived from dextran.

17. The method of claim 16, wherein the macromolecules comprise FITC dextran 150.

18. The method of claim 15, wherein the macromolecules comprise albumin.

19. The method of claim 18, wherein the macromolecules comprise FITC labeled albumin.

20. The method of claim 1, wherein the detectable marker is a fluorophore, a chromophore, or a radioactive substance.

21. An apparatus for displaying the quantity of detectable marker in a subject's circulation over time and determining the presence of capillary leak after introducing into the subject's circulation a pharmaceutically acceptable solution comprising biodegradable, nontoxic macromolecules, which are smaller than endothelial gaps of capillaries in a subject having capillary leak, and each of which macromolecules is labeled with a detectable marker, which apparatus comprises:

(a) means for obtaining samples of blood from the subject at a plurality of points in time;

(b) means for quantitively measuring the detectable marker in the sample obtained at each time point;

(c) means for determining the presence of capillary leak using the quantities so measured; and (d) means for displaying the presence of capillary leak and quantities of detectable marker measured.

* * * * *